United States Patent [19]

Van Der Ouderaa et al.

[11] Patent Number: 5,240,696
[45] Date of Patent: Aug. 31, 1993

[54] TREATMENT OF PERIODONTITIS

[75] Inventors: Franciscus J. Van Der Ouderaa, Neston; Diane Cummins, West Kirby; Derek M. Hull, Hawarden, all of Great Britain

[73] Assignee: Chesebrough-Pond's USA Co., Division of Conopco, Inc., Greenwich, Conn.

[21] Appl. No.: 926,073

[22] Filed: Aug. 5, 1992

[30] Foreign Application Priority Data

Aug. 8, 1991 [GB] United Kingdom ............... 9117140

[51] Int. Cl.$^5$ .................. A61K 7/16; A61K 33/30
[52] U.S. Cl. .................................. 424/49; 424/642
[58] Field of Search ........................ 424/49-58, 424/642

[56] References Cited

U.S. PATENT DOCUMENTS

| 4,287,191 | 9/1981 | Coburn et al. | |
| 4,358,443 | 10/1982 | Coburn et al. | |
| 4,522,806 | 6/1985 | Muhlemann et al. | 424/642 |
| 4,575,457 | 3/1986 | Mazarin | 424/49 |
| 4,664,906 | 5/1987 | Sipos | 424/49 |
| 4,742,083 | 5/1988 | Ritchey | |
| 4,961,924 | 10/1990 | Suhonen | 424/52 |
| 4,997,640 | 3/1991 | Bird et al. | 424/49 |
| 5,015,467 | 5/1991 | Smitherman | 424/49 |
| 5,094,842 | 3/1992 | Riley | 424/49 |

FOREIGN PATENT DOCUMENTS

| 0161898 | 11/1985 | European Pat. Off. . |
| 0295954 | 12/1988 | European Pat. Off. . |
| 0474597 | 3/1992 | European Pat. Off. . |
| 508524 | 10/1992 | European Pat. Off. . |
| 92/10994 | 7/1992 | PCT Int'l Appl. . |
| 1489672 | 10/1977 | United Kingdom . |
| 1550139 | 8/1979 | United Kingdom . |

OTHER PUBLICATIONS

C.A. 117:239515T (1992), EP. 50852y Oct. 14, 1992, Hughes et al.
Agents and Actions, vol. 29, No. 3/4 (1990), pp. 232-238 "Inhibition of human perodontal prostaglandin E$_2$ synthesis with selected agents".
J. Clin Periodontal, vol. 18, No. 6, Jul. 1991, pp. 462-467 and 468-473 and vol. 17, No. 8, 1990, pp. 570-574.
The Merck Manual, pp. 2104-2106 1987.
Colgate Brochure entitled, "PerioGard: Setting New Standards in Periodontal Care", specifically the page entitled: Colgate Gum Protection Formula Toothpaste, 1985.

Primary Examiner—Shep K. Rose
Attorney, Agent, or Firm—Milton L. Honig

[57] ABSTRACT

The present invention relates to the prevention of periodontitis by the use of a medicament which contains Triclosan. It has been found that Triclosan has a considerable anti-cyclo-oxygenase activity, thus inhibiting the formation of prostaglandins which are mediators of the loss of alveolar bone in the periodontium. Reducing the formation of said prostaglandins therefore reduces said loss of alveolar bone, which is one of the symptoms connected with periodontitis.

The medicament is preferably in the form of a toothpaste.

3 Claims, No Drawings

TREATMENT OF PERIODONTITIS

The present invention relates to the prevention, inhibition and/or reduction of periodontitis by the use of a medicament that comprises Triclosan (=2',4,4'-trichloro-2-hydroxy-diphenyl-ether).

Periodontitis is a general term describing specific diseases affecting the gingiva and the supporting connective tissue and alveolar bone which anchor the teeth in the jaws. Periodontitis causes loss of connective tissue, resorption of alveolar bone and formation of periodontal pockets, and may lead to a loosening of the teeth, and ultimately to the loss of teeth.

Periodontal disease is mainly caused by specific anaerobic bacteria in the periodontal pockets. The destruction of the periodontal tissue is primarily caused by the indirect effects mediated by the host's reaction to the bacteria. Bacterial metabolites induce leucocyte chemotaxis which results in the inflammatory cells accumulating at the site of the bacterial challenge. Furthermore, bacterial metabolites induce the production of inflammatory mediators by leucocytic cells, in particular monocytes. Amongst these are local disease mediators such as metabolites of arachidonic acid, e.g. leukotrienes, prostaglandins and thromboxanes. Additionally, the loss of alveolar bone may be directly induced by pathogenic metabolites of bacteria, in particular proteolyte enzymes. Prostaglandins have been found to be particularly important in the metabolism and destruction of tissue and alveolar bone. Indeed, the production of prostaglandins in the periodontal tissues has been found to be an important mediator of the loss of alveolar bone in the periodontium; patients with periodontal breakdown show an elevated prostaglandin $E_2$ level both in the gingival tissue as well as in the crevicular fluid. Prostaglandins and thromboxanes are formed from arachidonic acid by an enzyme cascade, the first step of which is the cyclo-oxygenation by an enzyme called cyclo-oxygenase. Inhibiting the cyclo-oxygenase would inhibit the formation of prostaglandins and thus reduce alveolar bone loss, and indeed certain cyclo-oxygenase inhibitors, particularly non steroidal anti-inflammatory drugs such as indomethacin and flurbiprofen have been found to markedly reduce the resorption of alveolar bone.

We have now found that Triclosan has a considerable anti-cyclo-oxygenase activity, thus significantly inhibiting the formation of prostaglandins. Inhibiting the biosynthesis of the prostaglandins locally would thereby significantly inhibit or prevent alveolar bone resorption. Triclosan has been shown to be retained by gingival tissue both in vitro and in vivo following topical application.

In this respect, it is observed that in the prior art it has been suggested to treat periodontal diseases with a combination of a non steroidal anti-inflammatory drug and an antimicrobial agent, e.g. the combination of aspirin, indomethacin or phenylbutazone with an antibacterial quaternary ammonium compound, such as cetylpyridinium chloride or a bis-biguanide compound such as chlorhexidine digluconate (GB 1,489,672).

Similar combinations are disclosed in GB 1,550,139, wherein the non steroidal anti-inflammatory agent can be selected from various classes of such agents, including indomethacin, ibuprofen, diclofenac and so on.

In U.S. Pat. No. 4,742,083 it has been disclosed that certain substituted salicylamides demonstrate an anti-inflammatory and an antimicrobial action. These salicylamides have previously been proposed for inclusion in oral compositions as anti-plaque agents (U.S. Pat. No. 4,287,191 and U.S. Pat. No. 4,358,443). However, Triclosan has been found to be a much more potent anti-inflammatory agent than the preferred substituted salicylamides of these references (which are also stated to be prostaglandin synthetase inhibitors).

Consequently, the present invention relates to the use of Triclosan in the manufacture of a medicament for inhibiting prostaglandin-forming cyclo-oxygenase activity. More particularly, it relates to the use of Triclosan in the manufacture of a medicament for preventing or inhibiting alveolar bone resorption. It relates especially to the use of Triclosan as prostaglandin-forming cyclo-oxygenase inhibitor in the manufacture of a medicament for preventing or reducing periodontitis.

Triclosan is a well-known anti-bacterial agent, used i.a. in oral compositions to reduce or inhibit the growth of dental plaque. Its use to inhibit cyclo-oxygenase activity to prevent or inhibit alveolar bone resorption or periodontitis has not been indicated in the prior art as far as we know.

Since Triclosan also has anti-bacterial activity, it not only modulates the host response system by inhibiting cyclo-oxygenase activity, but also reduces the microbial challenge, thus having a highly desirable combined, dual effect to prevent or reduce periodontitis.

The Triclosan-containing medicament of the present invention can be manufactured in any form, suitable for administering the medicament to achieve the reduction or prevention of periodontitis. Such forms are tablets, capsules, pills, powders, granules, solutions, suspensions, salves, gels, pastes etc. Suitable forms for oral administration are toothpastes, mouthwashes, gels and the like. Also it is possible to formulate the medicament in forms, suitable for topical and buccal administration, e.g. for dosing in the pockets by special applications, such as irrigator fluids, flosses, chewing gum, lozenges, fibres (hollow and monolytic), adhesive strips, tooth picks and the like.

The amount of Triclosan used in the present invention may vary from 0.0001-5, preferably 1% by weight of the medicament.

The Triclosan is preferably used in an amount above its MIC-values for certain micro organisms occurring in the pockets, known to contribute to periodontitis such as strains from the genera Actinomyces, Bacteroides, Peptococcus, Peptostreptococeus, Veillonella, Actinobacillus, Eubacteria, Fusobacteria and Liptotrichia, e.g. *Bacteroides gingivalis, B. intermedius, Actinobacillus actinomycetemcomitans*. The MIC-value of Triclosan for the latter is 0.0005%, and for all the other species between 0.001 and 0.005%.

The medicament furthermore may comprise further, conventional ingredients, such as pharmaceutically acceptable carriers like starch, sucrose, polyols, surfactants, water or water/alcohol systems etc. When formulated into a dentifrice, such formulation may contain all the usual dentifrice ingredients. Thus, they may comprise particulate abrasive materials such as silicas, aluminas, calcium carbonates, dicalciumphosphates, hydroxyapatites, trimetaphosphates, insoluble hexametaphosphates and so on, usually in amounts between 5 and 60% by weight.

Furthermore, they may comprise humectants such as glycerol, sorbitol, propyleneglycol, lactitol and so on.

Surface-active agents may also be included such as anionic, nonionic, amphoteric and zwitterionic synthetic detergents. Examples thereof are sodiumlaurylsulphate, sodium dodecylbenzenesulphonate, sodium mono- and dioctylphosphate, sodiumlauroylsarcosinate.

Binders and thickeners such as sodium carboxymethylcellulose, xanthan gum, gum arabic etc. may also be included, as well as synthetic polymers such as polyacrylates, copolymers of polyvinylmethylether with maleic anhydride. Flavours such as peppermint and spearmint oils may also be included, as well as preservatives, opacifying agents, colouring agents, pH-adjusting agents, sweetening agents and so on.

Other anti-bacterial agents may also be included such as chlorhexidine, copper-, zinc- and stannous salts, sanguinarine extract, metronidazole; furthermore anti-inflammatory agents such as ibuprofen, flurbiprofen, aspirin, indomethacin etc. may also be included. In this respect it has been found that the combination of Triclosan and a zinc salt such as zinc citrate markedly further improves the reduction of alveolar bone loss. The amount of zinc salt used may vary from 0.05 to about 10% by weight, calculated as zinc ion.

Anti-caries agents such as sodium- and stannous fluoride, aminefluorides, monosodiumfluorophosphate, casein and casein digests may also be included. Vitamins such as Vitamin C, plant extracts, potassium salts such as potassium citrate and potassium nitrate can also be included.

Other examples of additional anti-bacterial agents are quaternary ammonium compounds such as cetylpyridinium chloride; bis-guanides such as chlorhexidine digluconate, hexetidine, octenidine, alexidine.

Other anti-plaque agents include enzymes such as dextranase and/or mutanase, amyloglucosidase, glucose-oxidase with lactic oxidase, neuro amidases, hydrogenperoxide generating compounds such as potassiumperoxydiphosphate.

The following Examples illustrate the invention.

EXAMPLE 1

In vitro experiments were carried out to determine the $I_{50}$ value of various cyclo-oxygenase inhibitors. The $I_{50}$ value is the concentration of inhibitor which gives 50% inhibition of cyclo-oxygenase activity. These experiments were carried out as described in the general method given below, keeping the enzyme and substrate concentrations constant and using increasing inhibitor concentrations. Determinations at each inhibitor concentrations were carried out in duplicate.

The cyclo-oxygenase assay was carried out according to the method described by van der Ouderaa et al., "Methods in Enzymology" 86, page 60-68 (Academic Press Inc., 1982).

Reagents

Incubation buffer
0.1M Tris-HCl (pH 8.0) kept at 25° C. and continuously aerated by bubbling air through the solution.
8,11,14-eicosatrienoic acid stock solution
20 mg/ml in toluene kept under nitrogen at −20° C.
8,11,14-eicosatrienoic acid assay solution
0.5 ml of stock solution was taken and the toluene removed under a stream of nitrogen. The substrate was suspended in 10 ml of incubation buffer, freshly prepared each day and kept at room temperature.
Enzyme suspension stock
500 mg of dry lyophilized microsomal enzyme fraction, obtained from a 220,000 x g precipitate of a homogenate of sheep vesicular glands, was dispersed in 10 ml of incubation buffer for 5 min. using an Ultra Turrax homogeniser. The suspension was kept in ice throughout the experiment and shaken well before each sample was withdrawn.
Hydroquinone solution
0.23 mM in distilled water freshly prepared each day and kept on ice.
Hemin solution
0.1 mM made up in incubation buffer, freshly prepared each day and kept on ice.

GENERAL METHOD

The cyclo-oxygenase activity was measured at 25° C. by monitoring the oxygen consumption as a result of cyclo-oxygenation of the substrate using a Clark oxygen electrode.

A typical experimental run was carried out as follows. The enzyme suspension (100 µl), hydroquione solution (50 µl), hemin solution (50 µl) and buffer solution (to give a final volume of 2 ml) were pipetted into the incubation cell, followed by and appropriate volume of inhibitor solution (10–100 µl), if this was being used.

The mixture was then stirred for 5 min. to allow temperature equilibrium and to achieve a steady baseline on the chart recorder monitoring the dissolved oxygen concentration. Substrate solution (100 µl) was quickly injected into the cell to start the reaction and the oxygen consumption was typically monitored for 5 min. following addition of substrate.

The cyclo-oxygenase activity of the sample was calculated from the oxygen consumption curve assuming that maximum deflection of the recorder corresponds to 0.26 mM dissolved oxygen in the buffer and that 2 moles of oxygen are consumed per mole of substrate. The linear part of the sigmoid curve of oxygen consumption was used for initial-rate calculations.

The experiments were standardised by measuring the activity of the enzyme stock solution before and after each set of kinetic experiments and normalizing results to the mean activity.

The following inhibitors were used:
2′,4,4′ trichloro - 2-hydroxydiphenylether (Triclosan)
5-n-decanoyl-4′nitrosalicylanilide (AN-10)
5-n-octanoyl-′trifluoromethylphenyl-salicylanilide (APCF3-8)
sodium salicylate Triclosan was dissolved in ethanol; AN-10 and APCF3-8 were dissolved in polyethyleneglycol (MW 400) and sodium salicylate was used as an aqueous solution. The concentration of the inhibitor solutions were adjusted so that only 10 µl of the inhibitor solution was added. Blanks containing 10 µl of ethanol or polyethyleneglycol (MW400) showed no enzyme inhibition.

The following $I_{50}$ values for cyclo-oxygenase were measured:
compound: $I_{50}$
Triclosan: 155 µM
AN-10: 180 µM
APCF3-8: 240 µM
Sodium salicylate: 390 mM

EXAMPLE 2

Effect of Triclosan on Bone Loss in Vitro

Method

The experimental method used is fully described in Meghi,S et al. Brit. J. Cancer (1988) 58, pp 17-21. Neonatal mouse calvaria were isolated with minimum trauma and maintained in a nutrient medium appropriate for cell culture (DMEM+15% horse serum) at 27° C. in 100% humidity, the medium also containing the materials under test. The pH was maintained in an atmosphere of 5% $CO_2$. After 24 h the medium was discarded, the calvaria were divided into control and test groups, and the medium was replaced with fresh medium containing the materials under test. Prostaglandin $E_2$ ($PGE_2$, $10^{-6}M$) was added with or without Triclosan as appropriate to stimulate the release of calcium ions (i.e. bone resorption) from the calvaria. After two days further culture in the test media the release of calcium into the medium from the calvaria was determined by atomic absorption spectroscopy. Calcium release is a measure of bone resorption (i.e. degradation of bone) regulated by the specialised cells (osteoblasts and osteoclasts) on the bone surface. Net calcium release was obtained by subtracting the basal medium calcium level.

| Additions | Net Calcium Release (mg/dl) |
| --- | --- |
| None (negative control) | 0.4 |
| + $PGE_2$ (positive control) | 3.5* |
| + $PGE_2$ and $2.5.10^{-5}$ M Triclosan | −0.1* |
| + $PGE_2$ and $1.10^{-5}$ Triclosan | 1.4** |

(* P > 0.0001), (** P > 0.0005).

EXAMPLE 3

The test method of Example 2 was repeated, using thrombin, however, as bone loss stimulator, and using indomethacin as a cyclo-oxygenase inhibitor as control.

The following results were obtained:

| Additions | Net Calcium Release (mg/dl) |
| --- | --- |
| none | 0.2 |
| + thrombin | 3.9 |
| + thrombin and $10^{-6}$ M indomethacin | 0.4 |
| + thrombin and $5.10^{-5}$ M Triclosan | −0.6 |
| + thrombin and $1.10^{-5}$ M Triclosan | 0.2 |

EXAMPLE 4

The procedure of Example 3 was repeated, also using zinc citrate as addition.

The following results were obtained:

| Addition | Net Calcium Release (mg/dl) |
| --- | --- |
| none | 0.1 |
| thrombin | 2.4 |
| + thrombin and $10^{-6}$ M indomethacin | 0.0 |
| + thrombin and $2.10^{-4}$ M zinc citrate | 0.8 |
| + thrombin and $5.10^{-6}$ Triclosan | 0.75 |
| + thrombin and $2.10^{-4}$ M zinc citrate and $5.10^{-6}$ M Triclosan | −0.3* |
| + thrombin and $1.10^{-4}$ M zinc citrate | 1.3 |
| + thrombin and $5.10^{-6}$ M Triclosan | 0.75 |
| + thrombin and $1.10^{-4}$ M zinc citrate and $5.10^{-6}$ M Triclosan | −0.2* |
| + thrombin and $5.10^{-5}$ M zinc citrate | 1.4 |
| + thrombin and $5.10^{-6}$ M Triclosan | 0.75 |
| + thrombin and $5.10^{-6}$ M Triclosan and $5.10^{-5}$ M zinc citrate | −0.4* |

(* p < 0.05)

I claim:

1. A method for reducing alveolar bone loss leading to a loosening of the teeth and ultimately to the loss of the teeth by administering to the oral cavity of a subject afflicted with alveolar bone loss a composition containing an effective amount of a cyclo-oxygenase inhibitor, wherein the cyclo-oxygenase inhibitor is 2′,4,4′-tricholoro-2-hydroxy-diphenylether.

2. The method of claim 1, wherein the composition further comprises an effective antibacterial amount of zinc citrate.

3. The method of claim 1, wherein the composition is in the form of a dentrifice.

* * * * *